(12) United States Patent
Maffei et al.

(10) Patent No.: US 11,029,295 B2
(45) Date of Patent: Jun. 8, 2021

(54) VOCTRON: A LOW WEIGHT PORTABLE AIR SAMPLING DEVICE

(71) Applicant: Tintoria Piana US, Inc., Cartersville, GA (US)

(72) Inventors: Massimo Maffei, Turin (IT); Andrea Piana, Cartersville, GA (US)

(73) Assignee: TINTORIA PIANA US, INC., Cartersville, GA (US)

(*) Notice: Subject to any disclaimer, the term of this patent is extended or adjusted under 35 U.S.C. 154(b) by 80 days.

(21) Appl. No.: 16/157,148

(22) Filed: Oct. 11, 2018

(65) Prior Publication Data
US 2020/0116691 A1    Apr. 16, 2020

(51) Int. Cl.
| G01N 33/00 | (2006.01) |
| G01N 33/497 | (2006.01) |
| G01N 1/22 | (2006.01) |
| G01N 30/72 | (2006.01) |

(52) U.S. Cl.
CPC ....... *G01N 33/0047* (2013.01); *G01N 1/2205* (2013.01); *G01N 1/2273* (2013.01); *G01N 33/497* (2013.01); *G01N 1/2214* (2013.01); *G01N 30/7206* (2013.01); *G01N 2001/2244* (2013.01)

(58) Field of Classification Search
CPC ............... G01N 1/2214; G01N 1/2273; G01N 33/0047; G01N 2001/2244; G01N 2033/4975; G01N 1/2205; G01N 30/7206; G01N 33/497; G01N 2030/025
See application file for complete search history.

(56) References Cited

U.S. PATENT DOCUMENTS

| 4,858,476 | A | * | 8/1989 | Tobin | G01N 1/2273 73/863.23 |
| 4,909,090 | A | * | 3/1990 | McGown | G01N 1/2214 73/864.33 |
| 5,168,068 | A | * | 12/1992 | Yanagisawa | G01N 1/2273 422/416 |
| 7,010,991 | B2 | * | 3/2006 | Lutz | G01N 1/2205 73/864.33 |
| 7,422,909 | B2 | * | 9/2008 | Schur | G01N 1/2273 436/177 |
| 7,600,439 | B1 | * | 10/2009 | Patterson | G01N 1/405 73/23.37 |
| 7,841,244 | B2 | * | 11/2010 | Barket, Jr. | G01N 1/2214 73/862.21 |

(Continued)

OTHER PUBLICATIONS

Sethi et al., "Clinical Application of Volatile Organic Compound Analysis for Detecting Infectious Diseases", Clinical Microbiology Reviews, vol. 26, No. 3, p. 462-476 (Jul. 2013).

(Continued)

*Primary Examiner* — Justin N Olamit
(74) *Attorney, Agent, or Firm* — W&C IP

(57) ABSTRACT

A low weight portable air sampling device comprising a housing at least partially enclosing an inlet for receiving an air or breath sample; a removable liner coupled to the inlet containing sorbing materials; a micro-pump for regulating air flow within the device; and an outlet for emitting the air or breath sample from the device is described. The device may be used to collect Volatile Organic Compounds (VOCs) of both biotic and abiotic origin.

24 Claims, 19 Drawing Sheets

(56) References Cited

U.S. PATENT DOCUMENTS

| | | | |
|---|---|---|---|
| 8,479,355 B2* | 7/2013 | Kara | A47L 9/19 |
| | | | 15/339 |
| 9,063,040 B2* | 6/2015 | Calio | G01N 1/26 |
| 10,175,198 B2* | 1/2019 | Briglin | G01N 27/64 |
| 10,663,454 B2* | 5/2020 | Godula-Jopek | B01D 46/0005 |
| 2005/0266415 A1* | 12/2005 | Ryan | C12Q 1/04 |
| | | | 435/6.19 |
| 2007/0062255 A1 | 3/2007 | Talton | |
| 2007/0272852 A1 | 11/2007 | Raanan et al. | |
| 2010/0281891 A1* | 11/2010 | Behrends | B01D 53/26 |
| | | | 62/85 |
| 2014/0242601 A1 | 8/2014 | Belbruno | |
| 2015/0289782 A1* | 10/2015 | Peverall | A61B 5/14532 |
| | | | 600/532 |
| 2017/0100057 A1* | 4/2017 | Wang | A61B 5/7278 |
| 2018/0172561 A1* | 6/2018 | Kocher | G01N 1/14 |

OTHER PUBLICATIONS

Garcia-Alcega et al., "Fingerprinting outdoor air environment using microbial volatile organic compounds (MVOCs)—A review", Trends in Analytical Chemistry 86 (2017) 75-83.

* cited by examiner

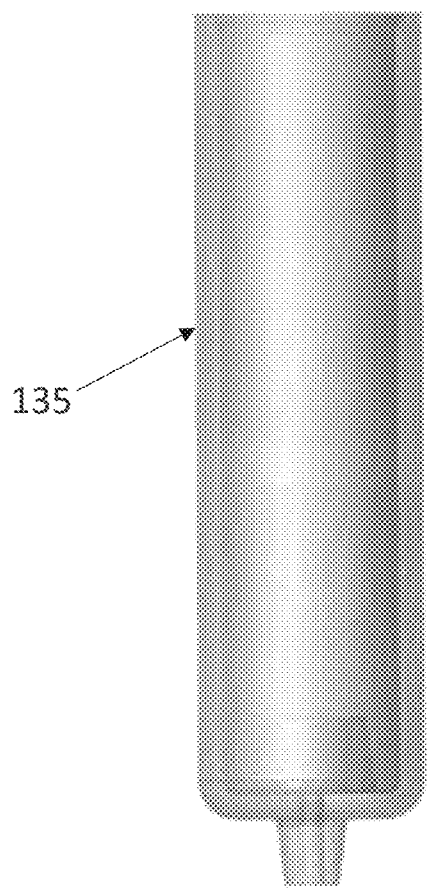 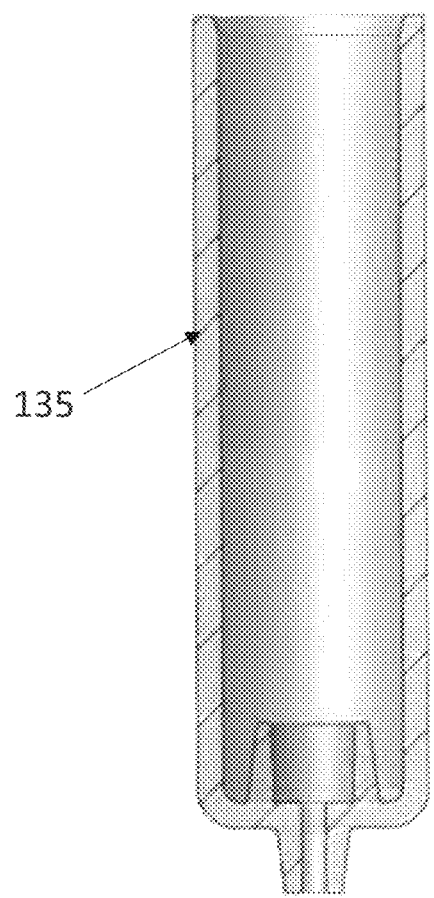
FIG. 3A
FIG. 3B

VOCTRON: A LOW WEIGHT PORTABLE AIR SAMPLING DEVICE

FIELD OF THE INVENTION

Embodiments of the invention provide a device for the sorption/adsorption of Volatile Organic Compounds (VOCs) of both biotic and abiotic origin.

SUMMARY OF THE INVENTION

The portable air sampling device, according to some embodiments of the disclosure, is a low weight device that contains an integrated system that allows for the sorption/absorption of VOCs generated by either living organisms (biotic origin) or by natural environmental situations (emission from industrial processes, natural or induced biodegradation, etc.), the latter being of both biotic and abiotic (not generated by living organisms) origin. The high capacity and sensitivity of the device for VOC trapping allows for air quality checking and breath sampling in numerous different environments while its low weight and long standing working ability provide ease of portability.

One aspect of the disclosure provides a portable air sampling device comprising a housing at least partially enclosing an inlet for receiving an air or breath sample; a removable liner coupled to the inlet containing sorbing materials; a micro-pump for regulating air flow within the device; and an outlet for emitting the air or breath sample from the device. In some embodiments the liner is made of borosilicate, PVC, Teflon or similar materials. In some embodiments, the inlet is defined by an open cavity passing through a removable cap. In some embodiments, the device further comprises an accessory attached to the inlet for receiving an air or breath sample selected from the group consisting of a mouthpiece, a plate for skin sniffing, a funnel, and a tube. In some embodiments, the mouthpiece is attached to the inlet and a filter for trapping moisture is arranged between the mouthpiece and the liner.

A portable air sampling device of the disclosure may further comprise a removable liner holder containing the liner. In some embodiments, the sorbing materials comprise one or more of silica gel, activated charcoal, porous polymers, polydimethylsiloxane, and porous anodic alumina. In some embodiments, the micro-pump is a miniature diaphragm pump. In some embodiments, the device further comprises a flow meter for measuring the air flow rate. In some embodiments, a display is used to show the air flow rate. In some embodiments, the device further comprises a master switch to operate the device. The master switch may have three positions: switched off, reduced flow, and full flow. In some embodiments, the outlet comprises a removable filter for trapping microorganisms. In some embodiments, a battery for is used to power the device. In some embodiments, a side of the housing includes a cavity for insertion of the removable liner and optionally the liner holder.

Another aspect of the disclosure provides a method for detecting VOCs present in a breath sample, comprising collecting a breath sample from a subject using a device according to the disclosure by i) positioning a mouthpiece connected to the inlet of the device to the mouth of the subject and ii) powering the device on for a predetermined time; removing the liner from the device; and desorbing VOCs adsorbed to the liner for analysis. In some embodiments, a moisture filter is arranged between the mouthpiece and the liner and the moisture filter is replaced before and/or after the collecting step. In some embodiments, an exhaust filter is coupled to the outlet and the exhaust filter is replaced before and/or after the collecting step. In some embodiments, a master switch having three positions: switched off, reduced flow, and full flow and the device is set to reduced flow during the collecting step. In some embodiments, the collecting step is performed for 20-30 minutes. In some embodiments, the liner is conditioned for reuse after the VOCs are desorbed. In some embodiments, analysis of the VOCs comprises gas chromatography coupled to mass spectrometry and gas chromatography coupled to Flame Ionization Detector or other detectors.

Additional features and advantages of the invention will be set forth in the description below, and in part will be apparent from the description, or may be learned by practice of the invention. The advantages of the invention can be realized and attained by the exemplary structure particularly pointed out in the written description and claims hereof as well as the appended drawings.

BRIEF DESCRIPTION OF THE DRAWINGS

FIGS. 3A-B. (A) A liner holder according to some embodiments of the disclosure. (B) A cross-sectional view of the liner holder in (A).

(B) A side cross-sectional view of the cap in (A).

Figures 6A, 6B:
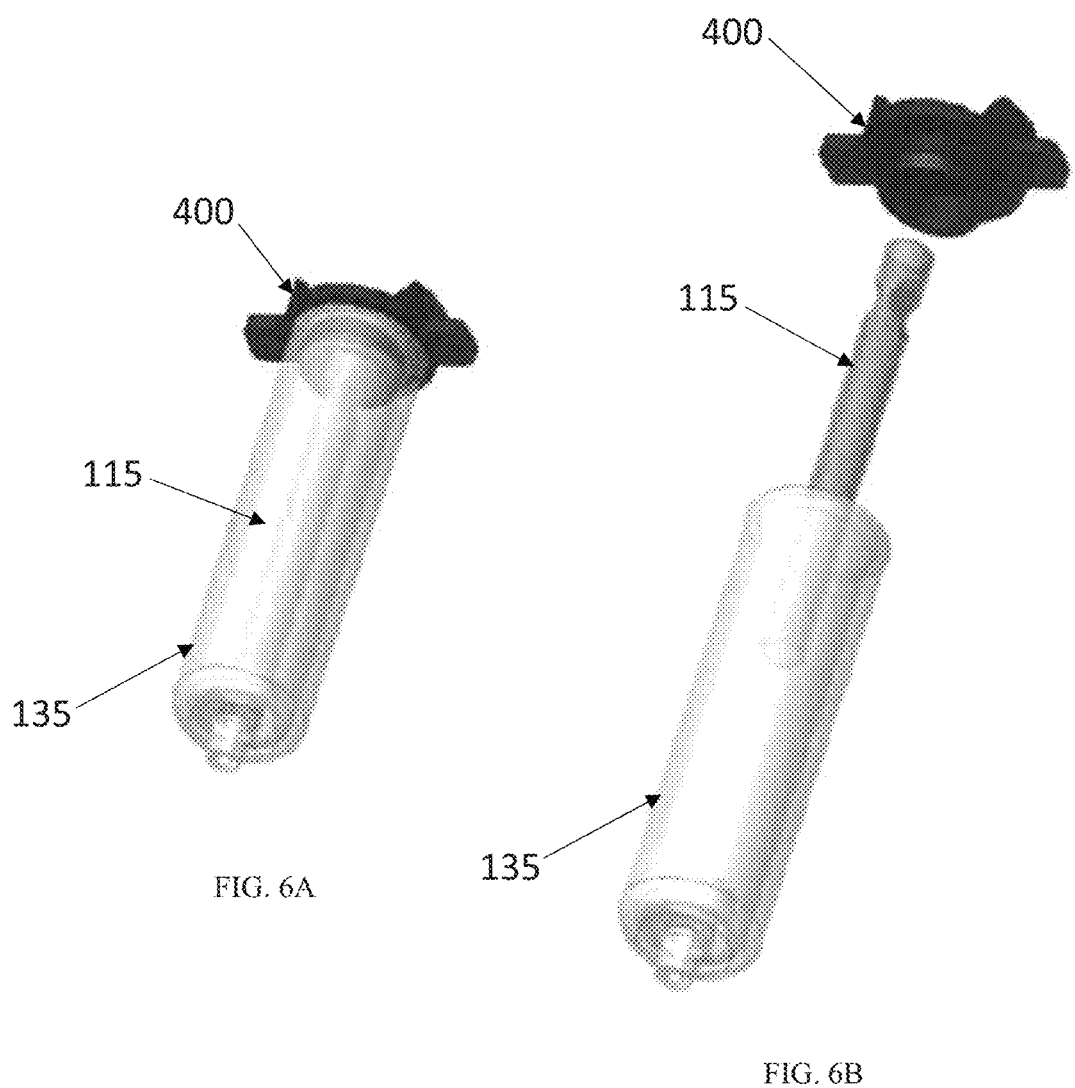

FIGS. 6A-B. (A) An assembled liner, liner holder, and cap according to some embodiments of the disclosure. (B) An exploded view of the assembly in (A).

Figure 7A:
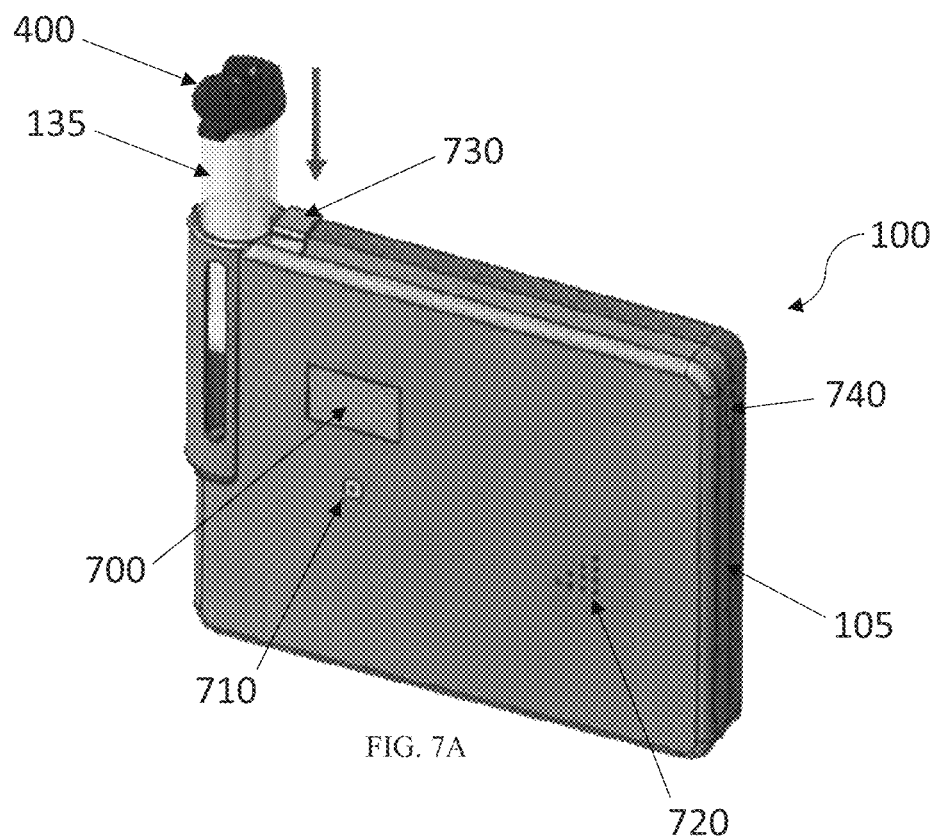
Figure 7B:
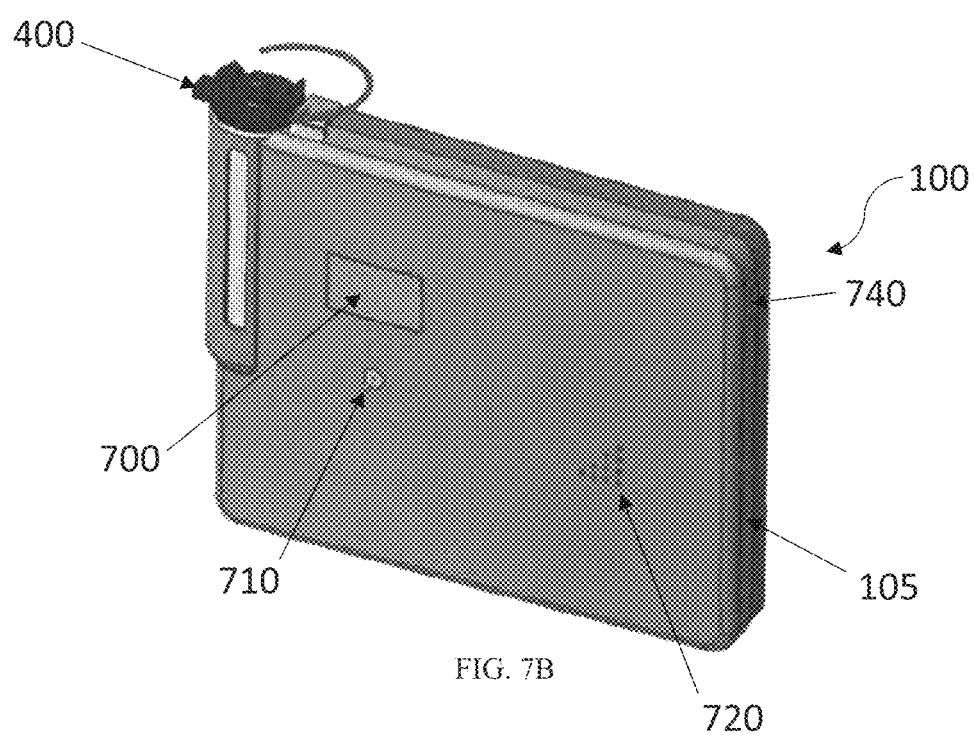

FIGS. 7A-B. (A) An exemplary assembled liner, liner holder, and cap partially inserted into the housing of a device according to some embodiments of the disclosure. (B) The assembled liner, liner holder, and cap of (A) fully inserted into the housing of a device according to some embodiments of the disclosure.

Figure 8A:
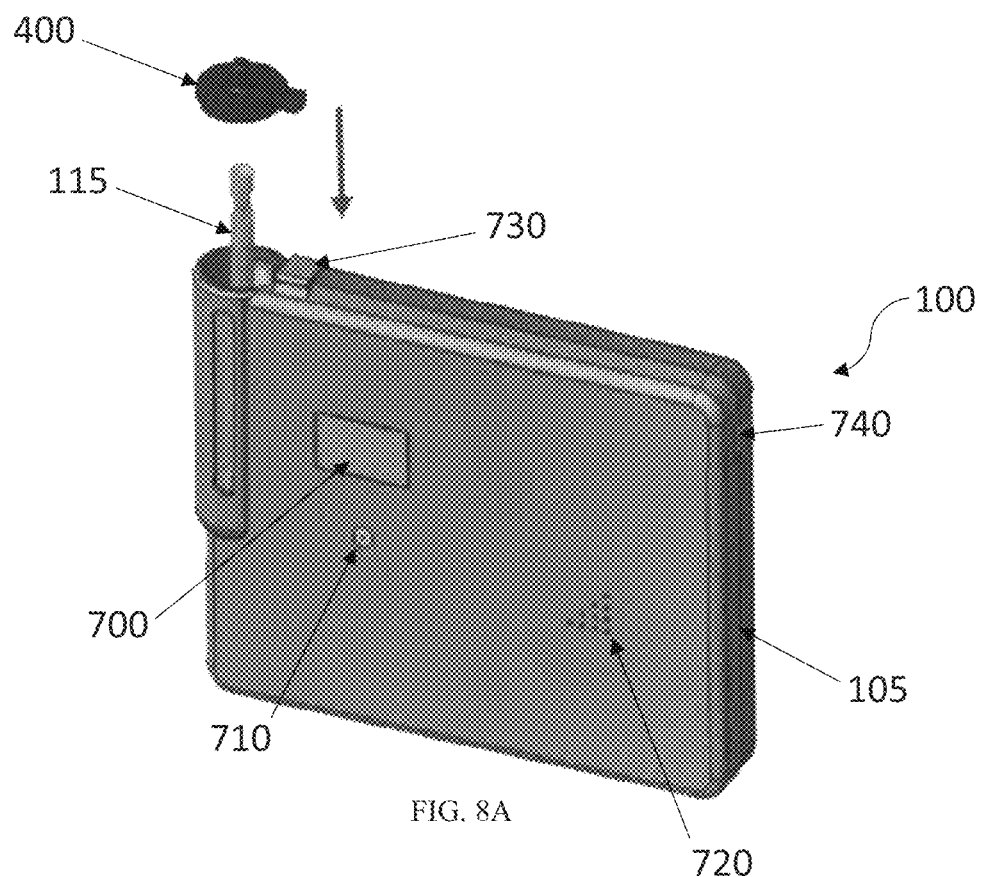
Figure 8B:
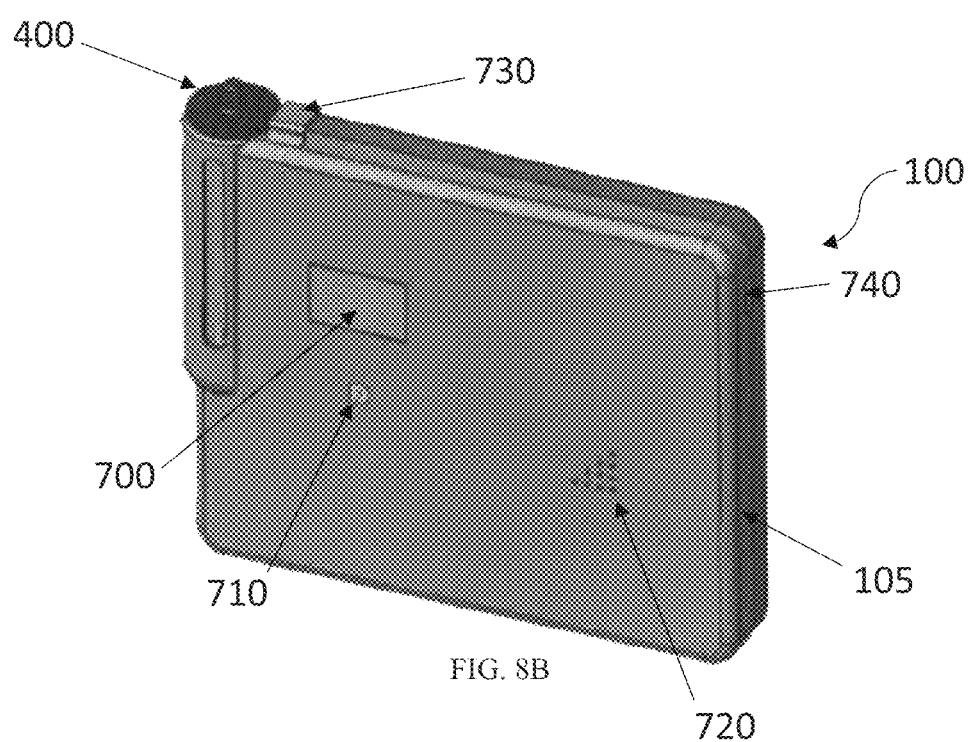

FIGS. 8A-B. (A) An exemplary liner and cap partially inserted into the housing of a device according to some embodiments of the disclosure. (B) The assembled liner and cap of (A) fully inserted into the housing of a device according to some embodiments of the disclosure.

Figures 9A, 9B:
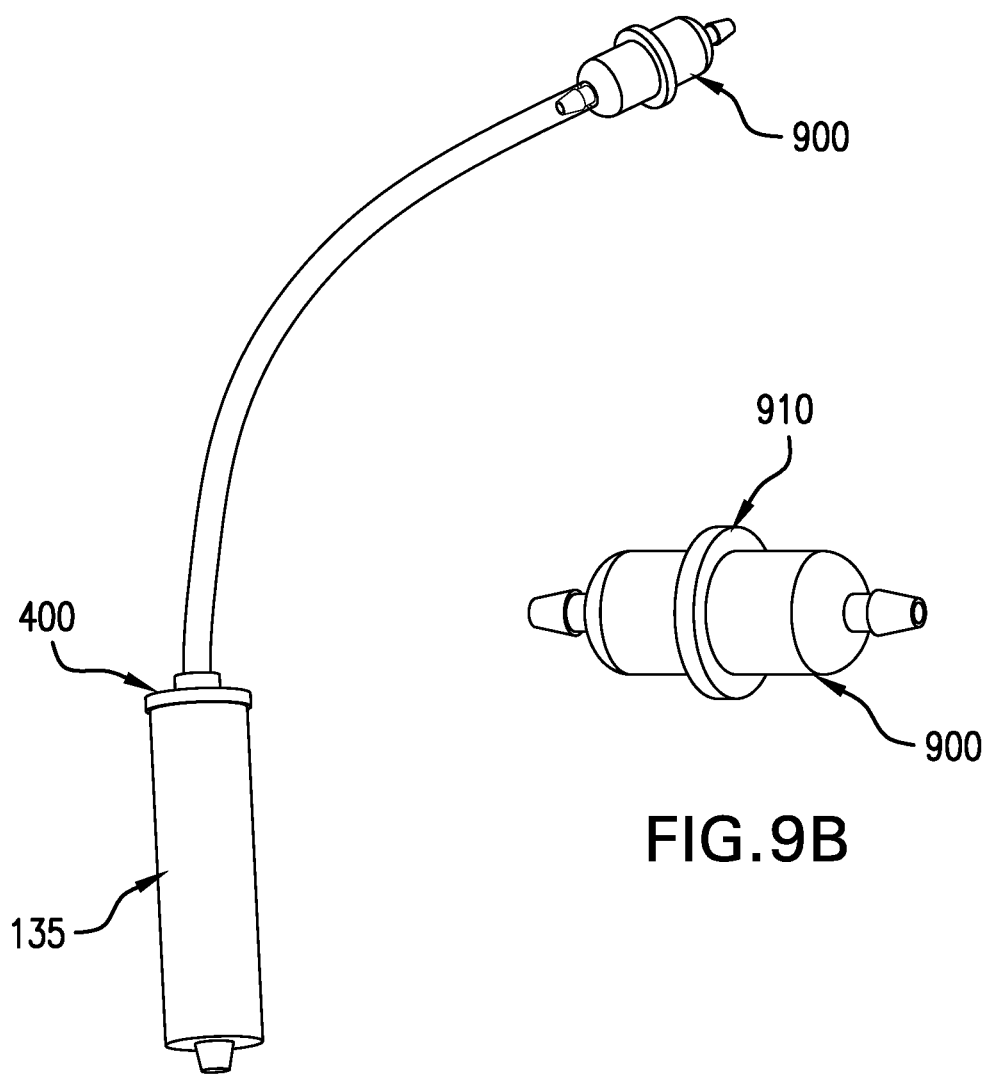
Figure 10A:
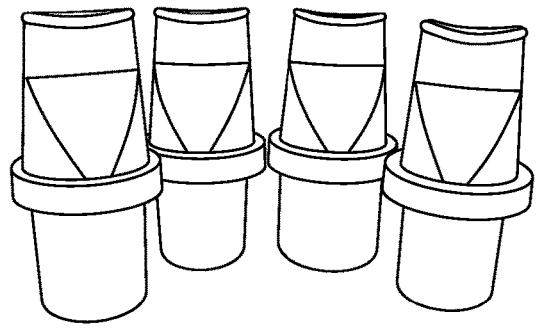
Figure 10B:
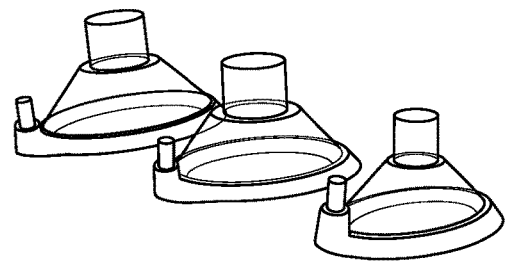
Figure 10C:
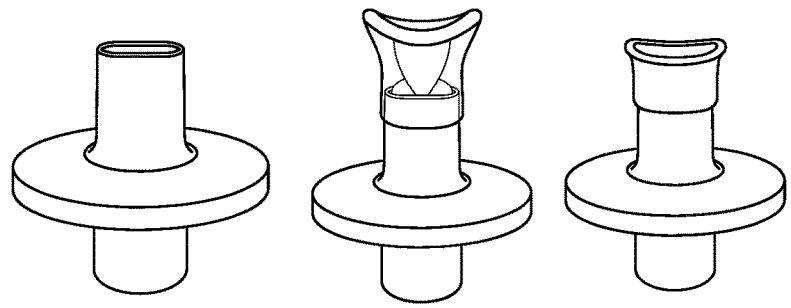
Figure 10D:
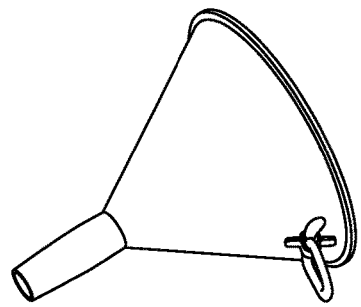

FIGS. 9A-B. (A) An exemplary mouthpiece connected to the inlet of an assembled liner, liner holder, and cap according to some embodiments of the disclosure. (B) A close-up view of the mouthpiece of (A).

FIGS. 10A-D. Air sampling accessories. Exemplary mouthpieces (A-C) and funnel (D) that are compatible with a device according to some embodiments of the disclosure.

Figure 11:
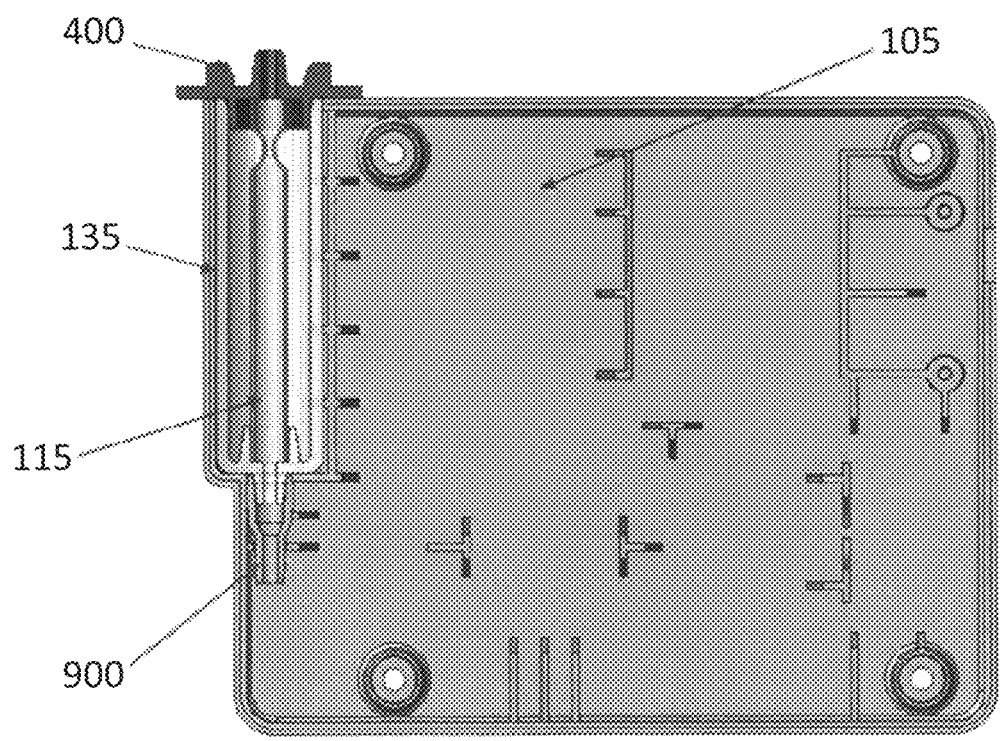

FIG. 11. A cutaway view of an assembled liner, liner holder, and cap inserted into the housing and a connector attached to the bottom of the liner holder according to some embodiments of the disclosure.

Figure 12A:
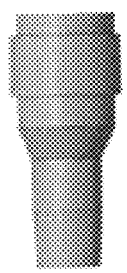
Figure 12B:
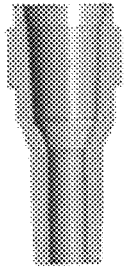

FIGS. 12A-B. (A) A connector as shown in FIG. 11 according to some embodiments of the disclosure. (B) A side cross-sectional view of the connector of (A).

Figure 13:
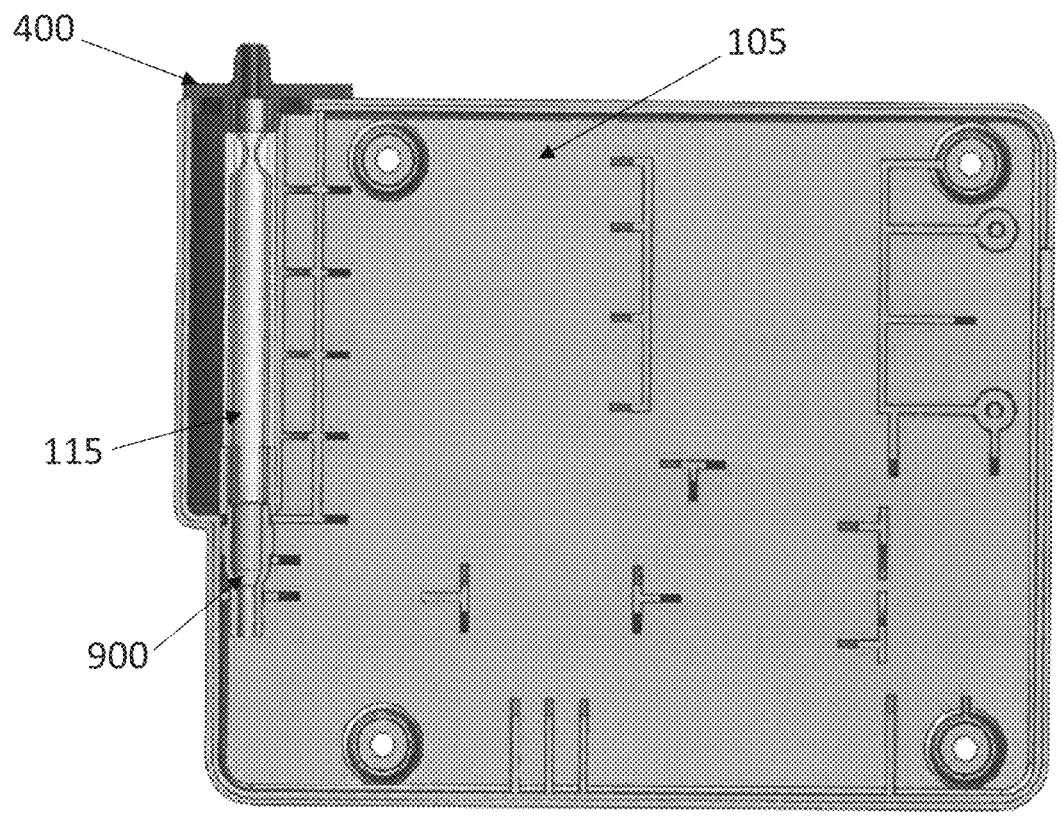

FIG. 13. A cutaway view of an assembled liner and cap inserted into the housing and a connector attached to the bottom of the liner according to some embodiments of the disclosure.

Figure 14A:
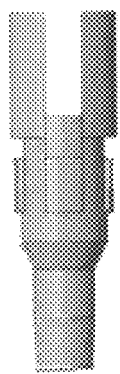
Figure 14B:
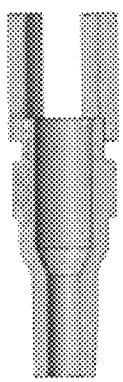

FIGS. 14A-B. (A) A connector as shown in FIG. 13 according to some embodiments of the disclosure. (B) A side cross-sectional view of the connector of (A).

Figure 15:
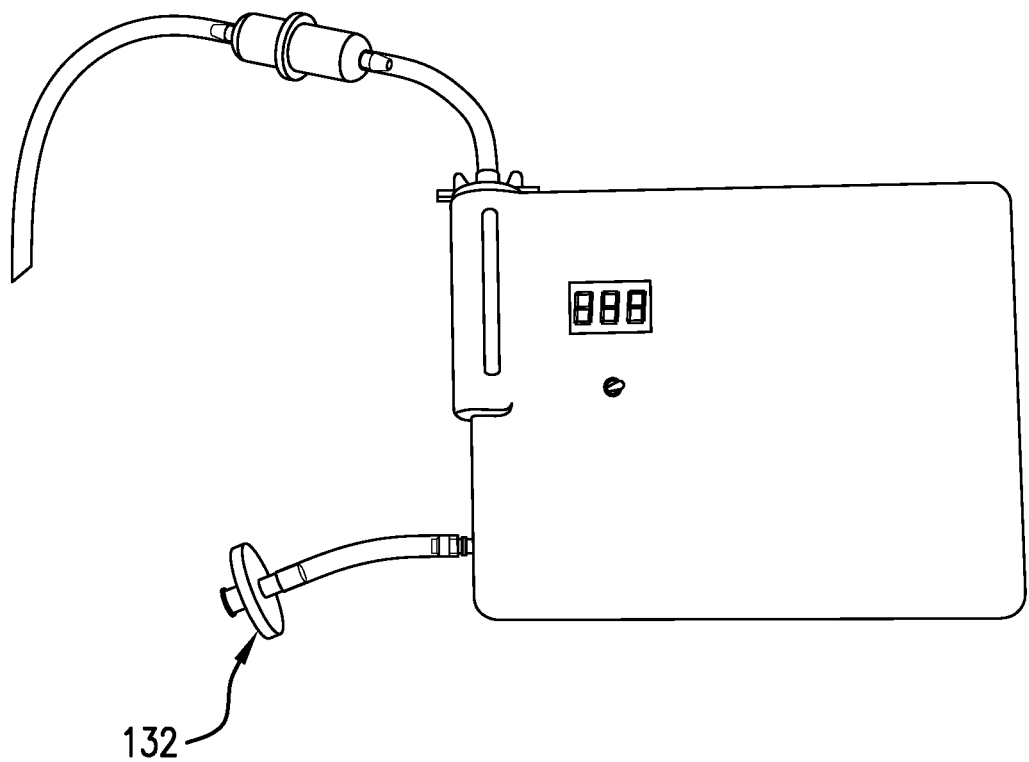
Figure 16A:
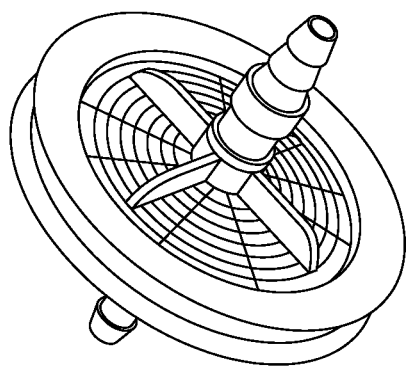
Figure 16B:
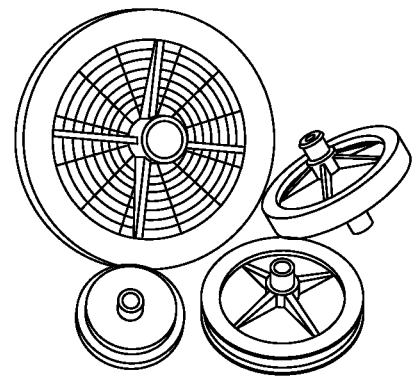
Figure 16C:
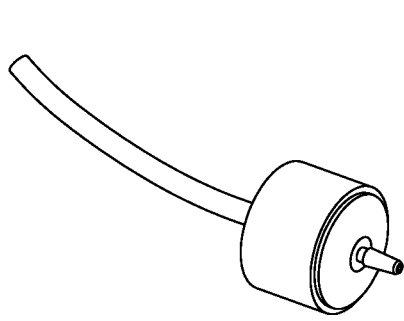
Figure 16D:
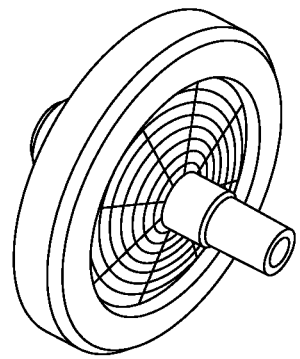

FIG. 15. An exemplary device comprising an exhaust filter according to some embodiments of the disclosure.

FIGS. 16A-D. (A-D) Exemplary exhaust filters that are compatible with a device according to some embodiments of the disclosure.

Figure 17:
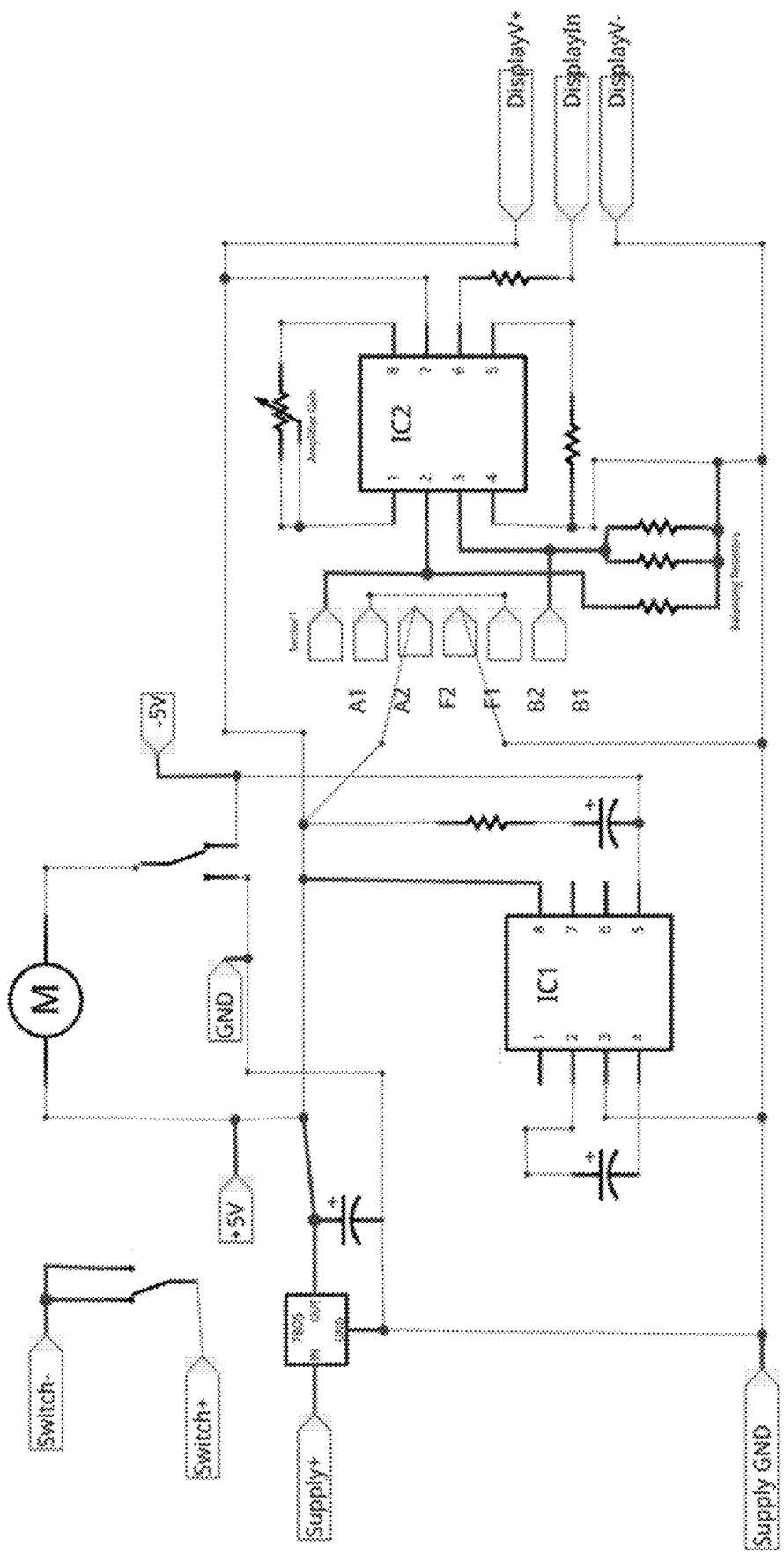

FIG. 17. Schematic of an electronic circuit according to some embodiments of the disclosure.

Figure 18A:
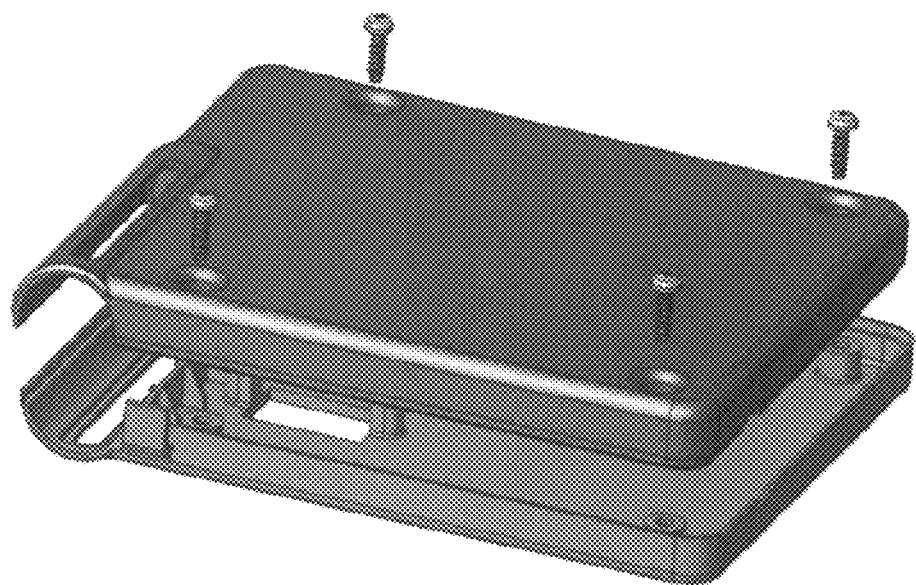
Figure 18B:
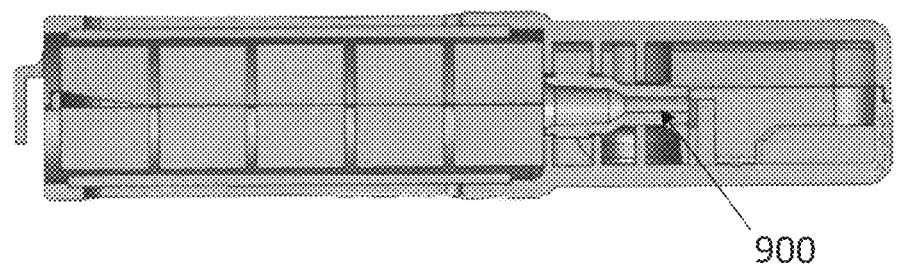

FIGS. 18A-B. (A) An exploded view of two portions of the housing and the screws used to secure the housing according to some embodiments of the disclosure. (A) A side cross-sectional view of the assembled housing of (A).

Figure 19:
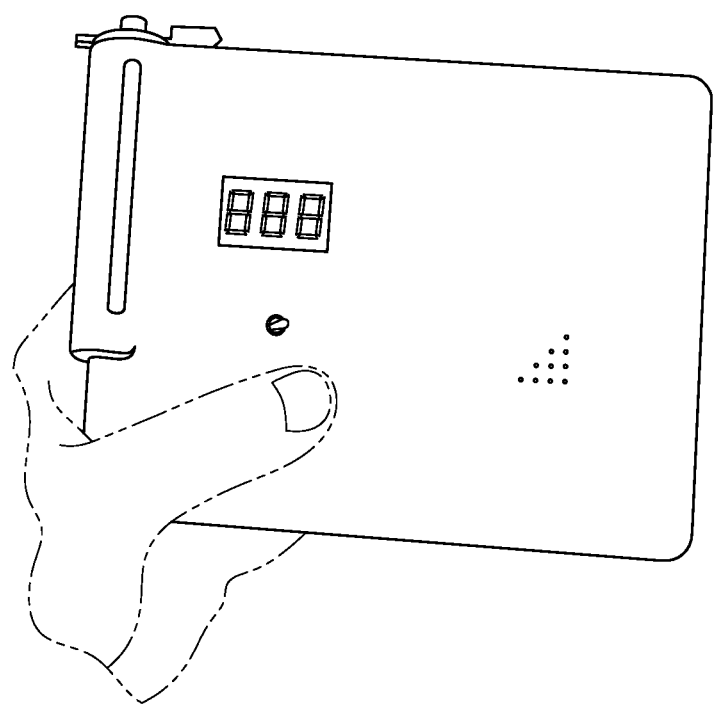

FIG. 19. An assembled portable device according to some embodiments of the disclosure.

Figure 20:
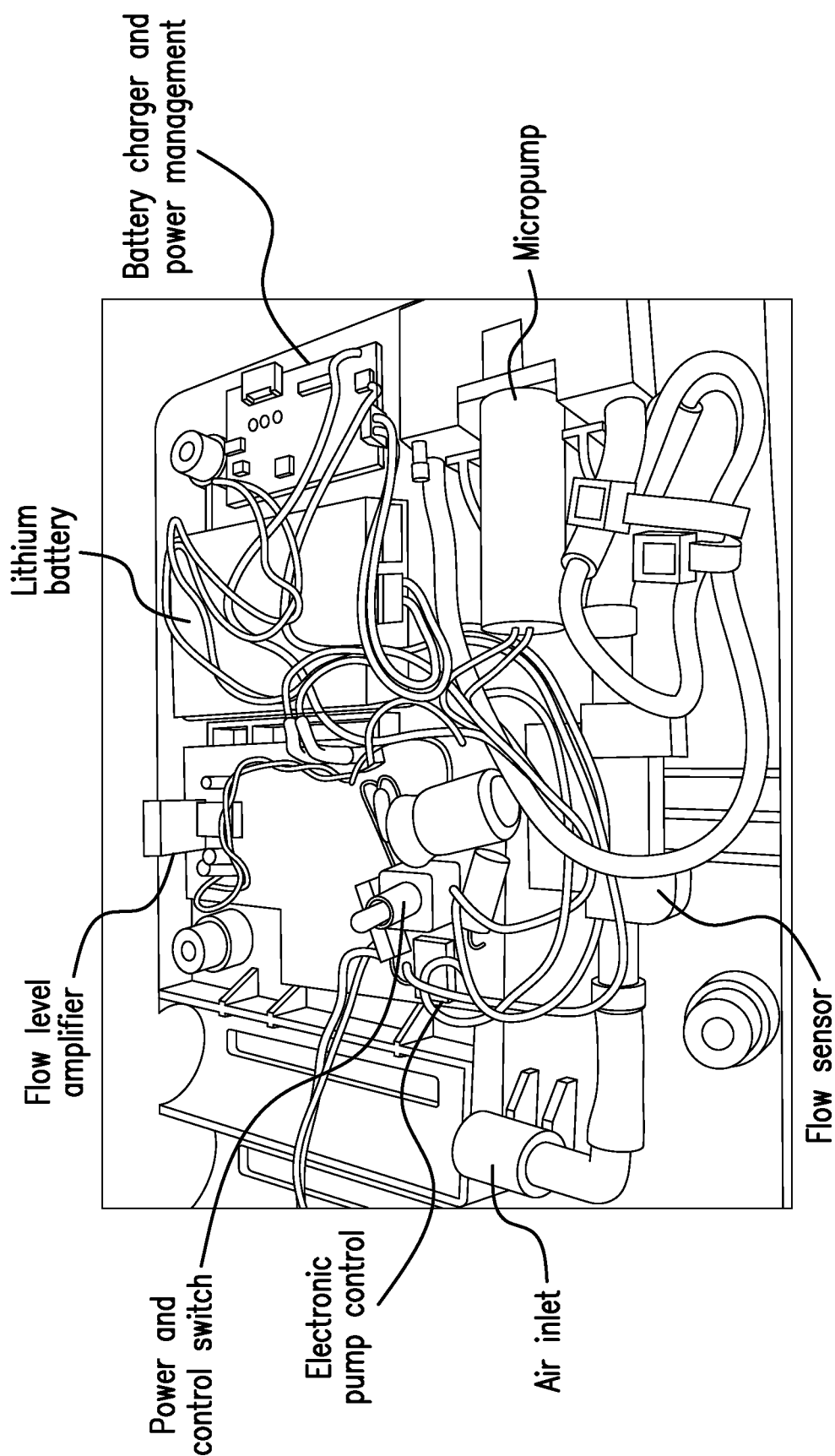

FIG. 20. A portable device according to some embodiments of the disclosure having a portion of the housing removed to display an arrangement of the inner components.

DETAILED DESCRIPTION

Embodiments of the disclosure provide a portable air sampling device for use in disease diagnosis, as well as drug and environmental monitoring. In particular, the device may detect VOCs emitted by living organisms (bacteria or their catabolic activities) present in the environment. When used in human beings, the device sorbs/adsorbs the VOCs produced by pathogenic microorganisms present in an individual, e.g. via the breath or by sampling the air around the individual, that are indicative of certain disease states. For example, microbial volatile organic compounds (MVOCs) are produced by a wide array of microorganisms ranging from bacteria to fungi and provide vital information regarding microbial activities. When used for the detection of the environment, the device can be used to assess the quality of air being able to sorpt/absorb Environment Volatile Organic Compounds (EVOCs) as in the case of air quality control in production plants (QCPP), in urban activities (UA, jogging, walking, etc.) and Environmental Protection quality assessment/assurance controls (EPQC).

A device of the disclosure provides a low weight system for volatile collection, including miniaturized components and a high capacity/sensitivity system for VOC trapping. The device has a lower weight and longer standing working ability than any other known device for VOC trapping. Indeed, prior systems that are designed for this use are typically 10 to 15 times heavier and lack portability. The device of the disclosure may be used in hospitals, clinics, or in one's home. The device is also suitable for environmental control, industrial air monitoring, military applications, etc.

Figure 1A:
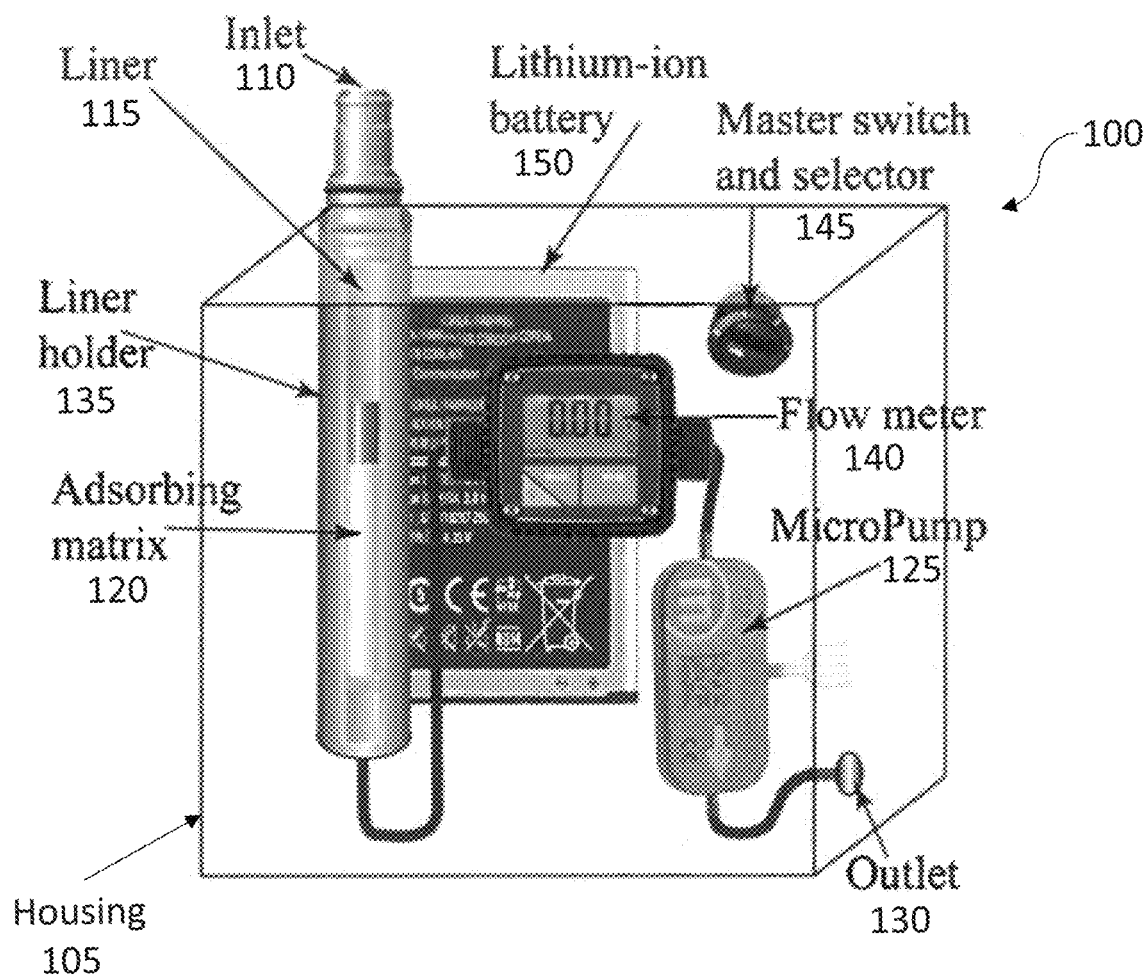
FIG. 1A-B. (A) Pictorial diagram and (B) flow diagram of a portable device according to some embodiments of the disclosure.
Figure 1B:
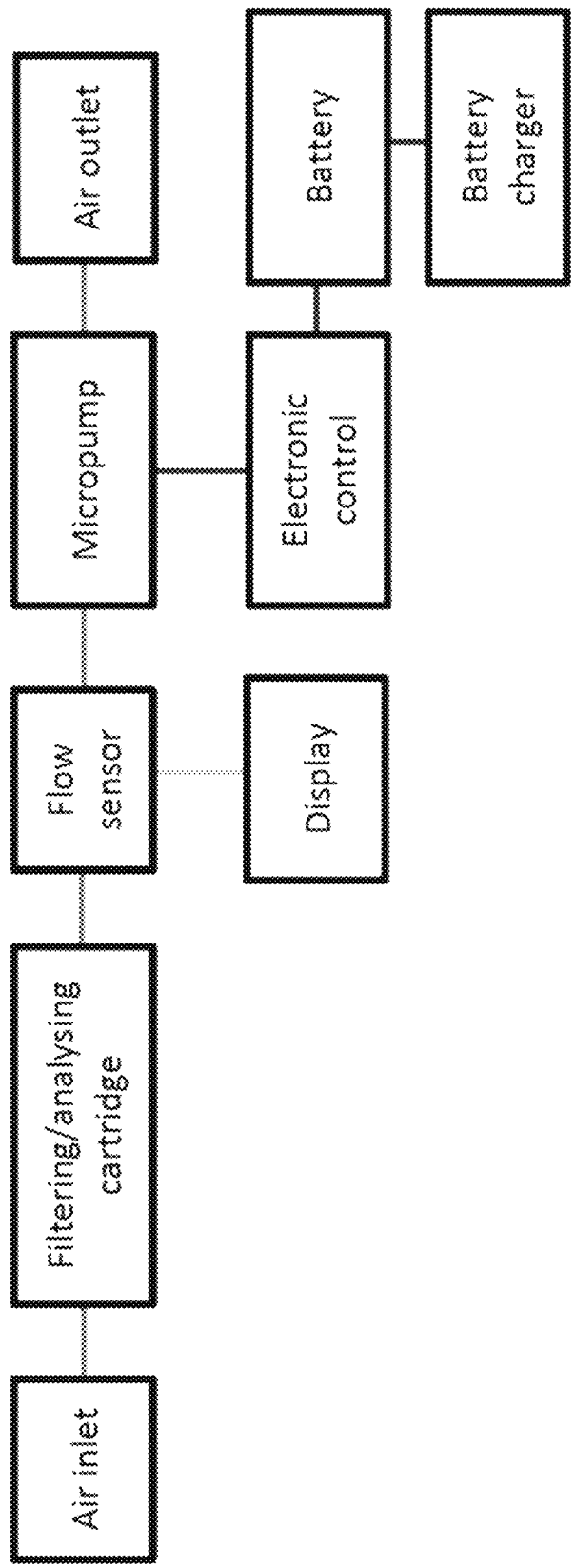

With reference to FIG. 1A-B, in some embodiments, a portable low weight air sampling device 100 comprises a housing 105 at least partially enclosing an inlet 110 for receiving an air or breath sample; a removable liner 115 coupled to the inlet 100 containing sorbing materials 120; a micro-pump 125 for regulating air flow within the device; and an outlet 130 for emitting the air or breath sample from the device.

By "low weight", it is meant that the device of the disclosure weighs less than about 5 pounds. In some embodiments, the device is less than about 3 pounds, less than about 2 pounds, less than about 1 pound, or less than about 0.5 pound. In some embodiments, the device is about 0.441 pounds or about 200 grams.

Figure 2:
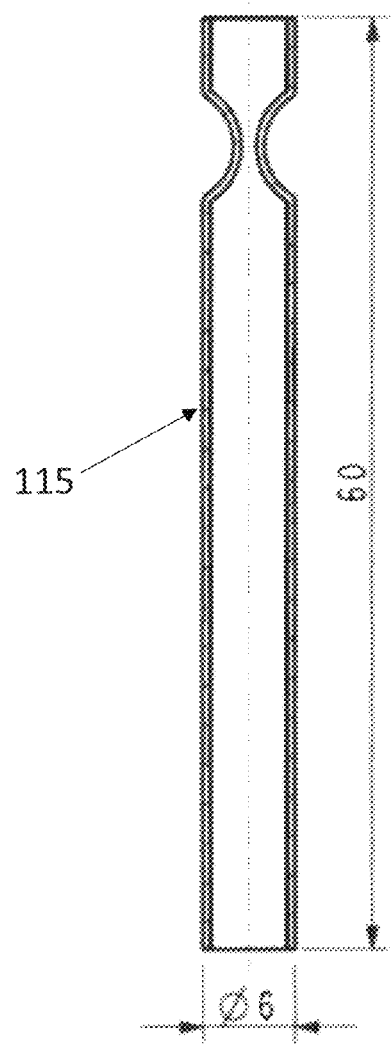
FIG. 2. A liner according to some embodiments of the disclosure. Dimensions are in millimeters.
Figure 4A:
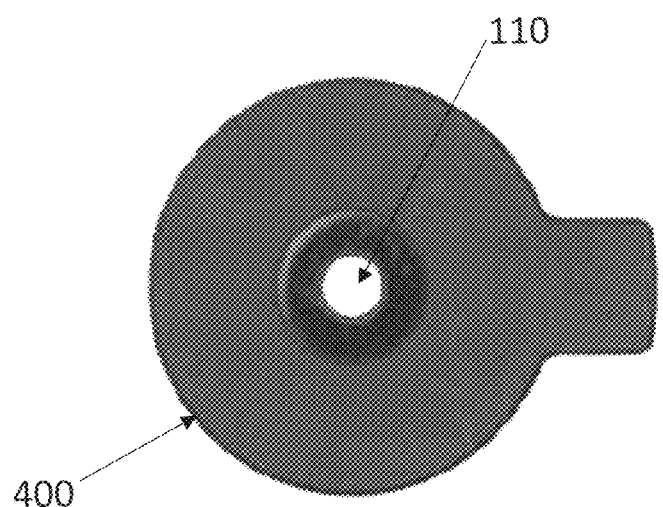
FIGS. 4A-B. (A) A top view of a cap according to some embodiments of the disclosure. (B) A side cross-sectional view of the cap in (A).
Figure 4B:
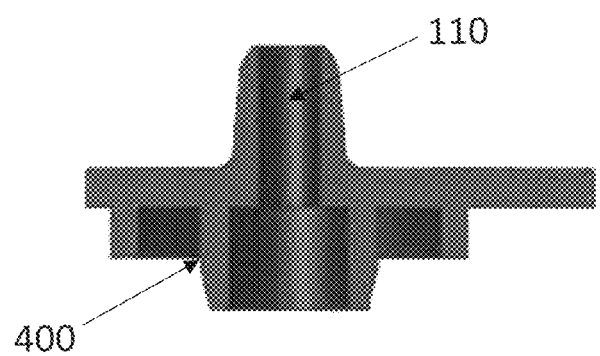
Figure 5A:
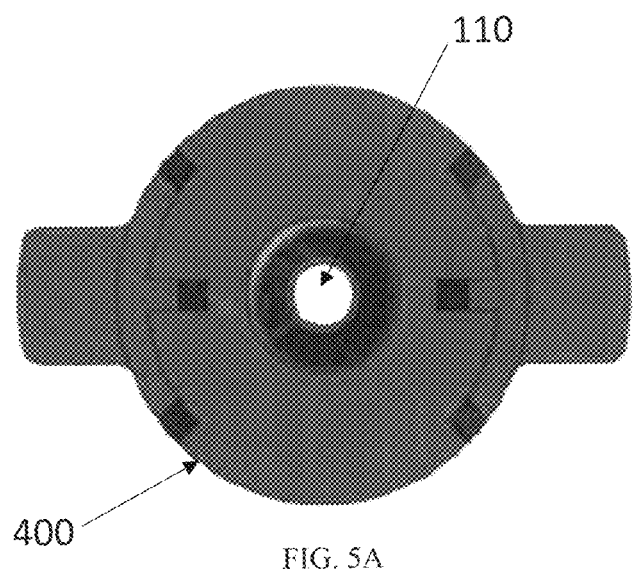
FIGS. 5A-B. (A) A top view of a cap according to some embodiments of the disclosure.
Figure 5B:
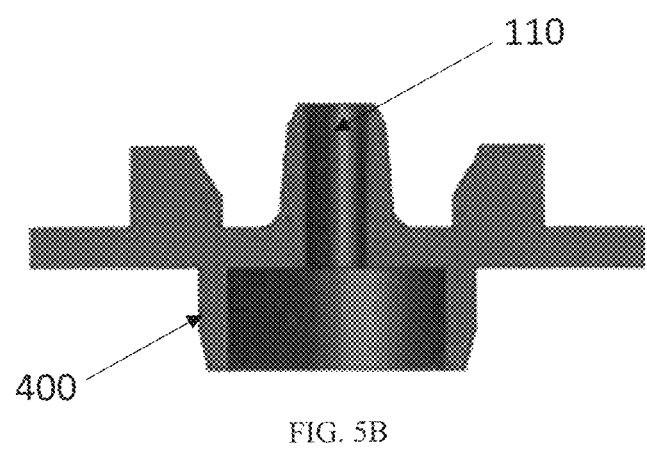

When an air sample enters the device, adsorbing/sorbing materials 120 contained within a liner 115 are used to trap/bind compounds (e.g. MVOCs, VOCs, EVOCs) based on differential sorption/adsorption of the compounds to the adsorbent/sorbent. The compounds are chemically bound in a dynamic mode to the adsorbing/sorbing matrix 120 contained in a liner 115 through head-space (HS). An exemplary liner 115 is shown in FIG. 2. For analysis of the compounds, the liner 115 is removed from the device and the compounds are desorbed from the matrix 120. For example, analytes may be isolated from the matrix 120 with or without using a liquid solvent, allowing fully automatic analysis systems in which sample preparation and analysis are integrated in a single step. In some embodiments, the compounds are desorbed using solvents or by thermal desorption through analytical methods such as gas chromatography coupled to either Flame Ionization Detectors (FID) or Mass Spectrometry Detectors (MSD) or by proton transfer reaction-mass spectrometry (PTR-MS).

Several adsorbing systems 120 are available for HS analysis of VOCs such as silica gel, activated charcoal, Anasorb® 747 and Carboxen®. The most commonly used in volatilome analyses, e.g. solid phase microextraction (SPME), are porous polymers. For example, in some embodiments, the adsorbing matrix 120 comprises a fiber coated with a sorbent material. Some systems are more suitable for solvent desorption, such as Chromosorb® 106, Amberlite® XAD-4, Porapak™ Q, and HayeSep® D, for example. With thermal desorption, the most commonly used sorbents are Tenax® TA, Carbotrap®, polydimethylsiloxane (PDMS), porous anodic alumina, and Carboxen®. The liner 115 may be composed of any suitable material such as borosilicate, glass, polycarbonate, plastic, or stainless steel. PDMS is ideal for detection of VOCs both in liquid phases and in gas phases with detection limits using mass selective detection in the low ng/L range for a wide selection of VOCs.

With reference to FIGS. 3-6, in some embodiments, the liner 115 is contained within a liner holder 135 which is connected to a cap 400. The liner 115 and liner holder 135 have an opening at the end opposite the cap 400 for the flow-through of air (FIG. 6A-B). In some embodiments, the liner holder 135 is disposable. In some embodiments, the liner holder 135 is transparent so that a user may monitor the adsorbing matrix 120 of the liner 115. In some embodiments, a side of the housing 105 includes a cavity (i.e. a filtering cartridge bay) for insertion of the removable liner 115 and optionally the liner holder 135.

With reference to FIGS. 7A-B, when the liner holder 135 is present, the cap 400 connects to the liner holder 135. With reference to FIGS. 8A-B, when the liner holder 135 is not present, the cap 400 connects directly to the liner 115. The cap 400 may have hole or junction for insertion of a tube, i.e. an inlet 100, to receive air samples from various air sampling accessories. In some embodiments, the cap 400 is disposable. In some embodiments, a raised protrusion 730 on the housing is used to secure the cap 400 in place by positioning an extended portion of the cap 400 under the raised protrusion 730. The cap 400 may have an extended portion on one (FIG. 4A-B) or two (FIG. 5A-B) or more sides of the cap.

Depending on the use of the device, different air sampling accessories known in the art may be attached to the cap 400, for example, via tubing. With reference to FIGS. 9A-B, a mouthpiece 900 for breath analysis may be attached to the cap 400 via a plastic tube. Suitable mouthpieces are known in the art (FIG. 10A-C), such as the spirometry mouthpieces sold by MADA of Milan, Italy. In some embodiments, a subject will inhale through their nose and exhale through their mouth into the mouthpiece 900. In other embodiments, the mouthpiece 900 includes an inlet for ambient air such that the subject can inhale and exhale from their mouth while the nose is clipped. In other embodiments, the mouthpiece 900 covers the nose and mouth. Additional examples of air sampling accessories include, but are not limited to, a wide plate for skin sniffing, a wide funnel for environmental air sampling (FIG. 10D), a tube for sampling restricted areas and for military and civil safety procedures, etc.

A filter 910 embodied, for example, in a plastic container may be included to trap moisture. In some embodiments, the filter is placed between the mouthpiece 900 and the MVOC trap, to reduce moisture and prevent saturation of the absorbent/sorbing material 120.

Portions of the device such as the liner holder 135, cap 400, and air sampling accessory may be disposable in order to limit either possible infections or contaminations. Single-use parts limits the potential transmission of infections agents to other patients.

With reference to FIG. 1A-B, the device may include a flow meter (or air flow sensor) 140 that transduces the air speed passing through the device into a voltage, proportional to the air flow rate. Exemplary flow meters are known in the art. The flow meter 140 may be used to measure linear, nonlinear, mass, or volumetric flow rate. The flow meter 140 may be contained within a plastic tube attached to the bottom portion of the liner holder 135 or the liner 115 via a connector 900 (FIGS. 11 and 13). The connector 900 may be held within the housing 105, for example, via ribs on the interior of the housing 105 (FIG. 16B) and is configured for removable attachment to the liner holder 135 (FIG. 12A-B) or the liner 115 (FIG. 14A-B). A digital LED voltmeter may be used to display the real-time flow data transduced by the flow meter 140. In some embodiments, the flow meter 140 is used as a controller for the master switch 710. An inverting charge pump may be used to increase the voltage. In embodiments where a subject exhales into the apparatus, either directly or via a mouthpiece, the flow meter 140 and one or more controllers is used to select a desired portion of a stream of breath exhaled into the sample inlet. This allows the device to select a particular portion of the breath, for example two or three hundred cubic centimeters from the end-tidal region of breath. The flow meter 140 can be, for example, a differential pressure transducer which can be adapted also to record the total volume of exhaled breath.

The micro-pump 125 establishes and regulates the air flow passing through the device. In some embodiments, the micro-pump 125 is able to sample from 1-1000 cc/min or higher. In some embodiments, the micro-pump 125 is a miniature diaphragm pump. Exemplary micro-pumps are known in the art. A diaphragm pump, also known as a membrane pump, is a positive displacement pump that uses a combination of the reciprocating action of a diaphragm and valves on either side of the diaphragm to pump a fluid such as gas. The diaphragm may be made from a rubber, thermoplastic, Teflon, or other suitable material. The valves may be check valves, butterfly valves, flap valves, or any other form of shut-off valves. The micro-pump 125 may allow a flow rate value within a 100 to 1000 ml/min range. The micro-pump 125 may be powered by an electronic regulator to produce an air flow through the device. A sensor then transduces and indicates the actual flow value.

A master switch 710, such as a toggle switch, may be used to control the device. In some embodiments, the switch 710 has three positions: switched off, reduced flow, and full flow. In the off state, the battery is disconnected however charging of the device is still allowed, e.g. through a micro USB charging port 740, and may be indicated by an LED. In some embodiments, two independent LEDs indicate the charging and operating status, e.g. in red and blue color respectively. In some embodiments, the center position of the switch is the "off" state and moving the switch to the right or left will turn the device on to a predefined flow level, e.g. reduced flow or full flow. In case of human sampling, the instrument may be set to reduced flow, e.g. set to a flow anywhere between 100-300 ml/min, whereas in case of environmental sampling the instrument may be set to full flow, e.g. set to a flow anywhere between 300-500 ml/min or higher. In some embodiments, the reduced flow is about 200 ml/min and the full flow is about 400 ml/min. In some embodiments, the flow may be controlled linearly (from very low to full flow) in order to calibrate the pump aspiration as a function of the required environment. When external air pressure is applied, the flow is subject to change, as stated by the numerical indication in the display.

A rechargeable battery 150, such as a lithium ion battery, may be used to power the device. In some embodiments, the battery 150 allows for up to 16 hours or more sampling time. In some embodiments, the battery 150 allows for at least four hours of continuous work. The battery 150 may include a USB output. In some embodiments, the battery is capable of being recharged through a standard USB cable connected to a charger or a hub. In some embodiments, the battery charger is a standard USB type Micro-B charger with an input voltage of 5 V. In some embodiments, the charger rated current is 500 mA. In some embodiments, the device includes a charger/booster such as a LiPo charger/booster to manage the battery charge when the device is connected to a power source.

All or some of the connectors and adaptation circuits for the connection of the electrical components of the device may be incorporated onto a printed circuit board (PCB).

In some embodiments, an air exhaust of the device, i.e. the outlet 130, may include an exhaust filter 132, such as a 0.2 μm filter, in order to trap bacteria or other microorganisms preventing their eventual delivery to the environment (FIG. 15). Exemplary filters that are compatible with the claimed invention are shown in FIGS. 16A-D. Such filters are commercially available, such as the Pall Acro® filters.

An exemplary electronic circuit of a device according to the disclosure is show in FIG. 17. The electronic circuit may be divided into three main sub-devices: a differential voltage amplifier, a led display and a charge-pump power supply converter. The fourth device on the circuit board is the air flow sensor. The sensor may be an air speed sensor that can be used in a suitable range of speed as a flow transducer. The sensor may be based on a modification of the hot wire technology: a low-power heater is placed in the middle of the device, while two temperature sensors are placed at the two sides. The very low voltages produced by the sensors share a common and constant DC level and produce opposite signals instead. In this situation, the measurement signal can be extracted without any superimposed DC voltage by connecting both sensors in anti-series. The two resulting terminals are then connected to the differential amplifier IC. Three balancing resistors can help to improve the null-flow offset of the amplifier in case of unbalance and one of the resistors can be cut to compensate the issue. A 1 MOhm trimmer can also substitute one of the resistors. In some embodiments, an integrated circuit encompasses all the above described functions.

The differential amplifier may be IC2 (type AD623). This circuit amplifies the mV-range signal of the flow sensor.

An adjustable gain trimmer may be provided. The IC may be a common low-noise, low-offset, high-Z operational amplifier. The output of the amplifier may be fed through a 10 kOhm resistor to the display unit input.

The display unit may be a modified voltage indicator. The analog input pin, normally connected to a voltage partition net coming directly from the same display power supply, allow to indicate the supply voltage, turning the display in a simple two-wire voltmeter. The same pin may be disconnected from the original net and tied to the device differential amplifier output, in order to display a number that is proportional to the transduced air flow level. Other three wire voltmeters or indicators can be effectively used in place of this solution that may be adopted due to the easy integration in the device.

With reference to FIG. 17, the sensor is represented in the schematic with six pins: A1 and A2 are the first cell output pins, F1 and F2 are the filament heater pins, and B1 and B2 are the second cell output pins. It has to be noted that the two cells are connected in series with opposite polarity, that is B2 tied with A2, in order to correctly cancel the DC voltage of each output. The pins tied to the amplifier input are consequently A1 and B1.

The charge pump converter, IC1 (type LT1054), is used to modify the supply voltage brought to the micropump. The pump may have a wide supply voltage range of 12 V dc. The pump free air flow (at zero differential pressure) is proportional to the supply voltage. Two different settings may be available for the free air flow, given by two different supply voltages: the lowest setting is achieved with the direct system voltage (5 V dc), while the higher setting required a voltage conversion. The LT 1054 integrated circuit is an inverting charge pump converter with feedback control. It is capable of providing a negative output of the same level, but opposite polarity, of the supply voltage. The output level setting can be changed, if necessary, by means of the correct feedback network. The mirrored negative level may be used. The higher flow level is obtained by powering the micropump with the positive and negative supplies. The resulting supply voltage is 10 V, except for subtle changes due to the converter regulation. A different voltage setting or a different monolithic charge-pump converter can fulfill the supply needs of a different micropump.

The power and flow selection switch may be a three position, central open, DPDT switch. One deviator may be connected as the main switch, providing the same power supply to the whole electronic board, regardless of the flow selection. The second deviator may be used to switch the low or high supply level to the micropump. In some embodiments, when the switch is in the center position the system is completely shut down, with negligible battery consumption. In this situation battery, charging is still possible. Moreover, the unit can also be operated during charging.

The battery charge controller and a suitable power supply converter may be placed on the same commercial board. The two devices may be completely separate, thus removing every influence between the device functionality and the battery charging.

The charge controller can manage the voltage level regulation from the USB port (5 V dc) to the lithium battery (nominally 3.7 V dc) according to the battery specifications.

The power supply converter can produce a stable 5 V dc power supply for the system, directly starting from the battery voltage. The converter may be of the non-isolated, step-up type and can reach very high efficiency levels when operating at sufficient current levels All or some of the components of the portable, i.e. hand-held, device may be enclosed in a casing or housing 105 (FIG. 19). In some embodiments, the overall dimensions of the device are less than about 150×150×50 mm. In some embodiments, the overall dimensions of the device are about 137×113×26 mm. The inside of the housing 105 may contain bosses and support ribs for the securement of the components. In some embodiments, the housing 105 is formed from two pieces, e.g. a front and back portion, which may be secured together, e.g. via bosses and self-tapping screws (FIG. 18A-B). Removal of the front portion of the housing may reveal an exemplary arrangement of the inner components of the device (FIG. 20). The front portion of the housing 105 may include openings for the display 700, e.g. an LCD screen, and the switch 710. The housing 105 may also include a plurality of holes 720 for the release of air from the pump. In some embodiments, all or some of the components of the device, e.g. the housing 105, may be 3D printed.

The device may be fabricated from polymeric materials such as medical grade polymers. In some embodiments, the materials do not contain phthalates. In some embodiments, the materials comply with regulations used for biocompatibility testing of medical devices such as the USP class VI or ISO 10993 standards. In some embodiments, the materials are suitable for sterilization, e.g. through heat, chemicals, autoclaving or irradiation. In some embodiments, the materials comprise polycarbonate/poly(ethylene terephthalate) (PC/PET) blends. In some embodiments, the liner holder is comprised of materials based on polyethylene terephthalate glycol (PETG), PC, and/or cyclic olefin copolymer (COC). In some embodiments, the cap is formed from thermoplastic elastomers such as thermoplastic vulcanizate (TPV).

A device of the disclosure may be used to analyze breath samples to diagnose diseases including, but not limited to, oral and lousy bowel diseases, periodontal diseases, respiratory and oral pathologies, gastrointestinal diseases, vaginal infections, and skin infections. A breath sample may comprise multiple compounds, including, but not limited to, MVOCs, alcohols, ethers, ketones, amines, aldehydes, carbonyls, carbanions, alkanes, alkenes, alkynes, aromatic hydrocarbons, polycyclic aromatics, hydrocarbons, biomolecules, isoprenes, isoprenoids, VOCs, VOAs, indoles, oxylipins, pyridines, fatty acids, and off-gases of a microorganism.

For example, methyl mercaptan and $H_2S$ have been associated with periodontal diseases. 2-aminoacetophenone, 2-pentylfurane, methyl phenylacetate, methyl p-anisate, methyl nicotinate, and o-phenylanisole are associated with respiratory and oral infections. Putrescine, cadaverine, and trimethylamine are associated with vaginal infections. 3-hydroxy-3-methylhexanoic acid and 3-methyl-2-esenoic acid are associated with skin infections.

In some embodiments, a device of the disclosure is used in a method for detecting VOCs present in a breath sample, comprising the steps of collecting a breath sample from a subject using the device by i) positioning a mouthpiece connected to the inlet of the device to the mouth of the subject; and ii) powering the device on for a predetermined time; removing the liner from the device; and desorbing VOCs adsorbed to the liner for analysis.

In some embodiments a device of the disclosure may be used in screening methods to determine VOC profile associated with selected diseases or disorders.

An example is provided for the detection of VOCs present in human breath:
1. The equipment is in Off position
2. The battery is charged
3. The liner containing the sorbent/adsorbing material is placed in the liner holder
4. The cap is closed over the liner holder
5. The moisture filter is replaced with a new one and the old one is disposed
6. The exhaust filter is replaced with a new one and the old one is disposed
7. The mouthpiece is replaced with a new one and the old one is disposed
8. The mouthpiece is positioned in touch with the mouth of the individual
9. The switch is set to "reduced flow" position
10. Sampling takes place for 20-30 min
11. The switch is set to off position
12. The operator removes the liner from the liner holder
13. The liner holder is saved for further GC-MS analyses
14. The liner can be reused after desorption and conditioning In some embodiments, one or more of the liner holder, the liner, and the cap are disposed after use. In some embodiments, one or more of the liner holder, the liner, and the cap are reused.

In some embodiments, the liner containing the sampled material can be directly inserted into a Thermal Desorbing Unit (TDU) connected to the injector port of either a GC-FID or a GC.MS apparatus. In some embodiments, the liner containing the sampled material can be directly subjected to solvent extraction by flushing hexane, cyclohexane, pentane, diethyl ether, dichloro methane, ethyl acetate, ethanol, a mixture of these solvents or other organic solvents, and the solute can be further analyzed by GC-FID, GC-MS or other gas-chromatographic methods. In some embodiments, after extraction of the analytes, the liner is conditioned by heating the liner at a high temperature, e.g. 250° C. under a permanent nitrogen flow (1 bar front pressure) for at least about 20 hours to remove impurities from the sorbent materials.

A device of the disclosure may also be used to detect EVOCs to assess QCPP including, but not limited to, airborne pollutants of organic nature, solvent residues, aldehydes, smoke and combustion volatile products, volatile organic oxides, volatile plastic derivatives (e.g., styrene, phthalates and bisphenol), bioeffluents (i.e., smell generated by human activities), air conditioning smells generated by MVOCs inside the pipes, etc. A device of the disclosure may be used to detect EVOCs to assess UA and EPQC including, but not limited to, assess the air quality index (AQI), a number used by government agencies to communicate to the public how polluted the air currently is or how polluted it is forecast to become during rush hour traffic or when there is an upwind forest fire, air pollutants concentration during temperature inversion, or low wind speeds, chemical reactions between air contaminants and hazy conditions, polycyclic aromatic hydrocarbon (PAH) detection, coal burning industries airborne pollutants, PM10- and PM2.5-airborne VOCs.

An example is provided for the detection of VOCs present in the environment:
1. The equipment is in Off position
2. The battery is charged
3. The liner containing the sorbent/adsorbing material is placed in the liner holder
4. The cap is closed over the liner holder
5. The moisture filter is replaced with a new one and the old one is disposed
6. The exhaust filter is replaced with a new one and the old one is disposed
7. The sampling tube is replaced with a new one and the old one is disposed
8. The sampling tube is connected to a plastic disposable funnel
9. The funnel is positioned toward the air space to be sampled
10. The switch is set to "full flow" position
11. Sampling takes place for 30-60 min
12. The switch is set to off position
13. The operator removes the liner from the liner holder
14. The liner holder is saved for further GC-MS analyses
15. The liner can be reused after desorption and conditioning It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A portable low weight air sampling device comprising:
a housing at least partially enclosing an inlet for receiving an air or breath sample, wherein the inlet is defined by an open cavity passing through and bounded by a removable cap;

a removable liner coupled to the cap such that the liner and the cap can be removed from the device as a single unit, wherein the removable liner contains sorbing materials;

a micro-pump for regulating air flow within the device; and an outlet for emitting the air or breath sample from the device.

2. The portable low weight air sampling device of claim 1, further comprising a removable liner holder containing the liner.

3. The portable low weight air sampling device of claim 1, further comprising an accessory attached to the inlet for receiving an air or breath sample selected from the group consisting of a mouthpiece, a plate for skin sniffing, a funnel, and a tube.

4. The portable low weight air sampling device of claim 3, wherein the mouthpiece is attached to the inlet and a filter for trapping moisture is arranged between the mouthpiece and the liner.

5. The portable low weight air sampling device of claim 1, wherein the sorbing materials comprise one or more of silica gel, activated charcoal, porous polymers, polydimethylsiloxane, and porous anodic alumina.

6. The portable low weight air sampling device of claim 1, wherein the micro-pump is a diaphragm pump.

7. The portable low weight air sampling device of claim 1, further comprising a flow meter for measuring the air flow rate.

8. The portable low weight air sampling device of claim 7, further comprising a display for showing the air flow rate.

9. The portable low weight air sampling device of claim 1, further comprising a master switch to operate the device.

10. The portable low weight air sampling device of claim 9, wherein the master switch has three positions: switched off, reduced flow, and full flow, wherein the full flow position is configured to provide a first predefined flow level and the reduced flow position is configured to provide a second predefined flow level that is lower than the first predefined flow level.

11. The portable low weight air sampling device of claim 1, wherein the outlet comprises a removable filter for trapping microorganisms.

12. The portable low weight air sampling device of claim 1, further comprising a battery for powering the device.

13. The portable low weight air sampling device of claim 1, wherein a side of the housing includes a cavity configured to hold the removable liner in place when the removable liner is inserted.

14. A method for detecting volatile organic compounds (VOCs) present in a breath sample, comprising:
collecting a breath sample from a subject using a device as claimed in claim 1 by
i) positioning a mouthpiece connected to the inlet of the device to the subject's mouth; and
ii) powering the device on for a predetermined time;
removing the liner from the device; and
desorbing VOCs adsorbed to the liner for analysis.

15. The method of claim 14, wherein a moisture filter is arranged between the mouthpiece and the liner and the moisture filter is replaced before and/or after the collecting step.

16. The method of claim 14, wherein an exhaust filter is coupled to the outlet and the exhaust filter is replaced before and/or after the collecting step.

17. The method of claim 14, wherein the device comprises a master switch having three positions: switched off, reduced flow, and full flow and the device is set to reduced flow during the collecting step.

18. The method of claim 14, wherein the collecting step is performed for 20-30 minutes.

19. The method of claim 14, wherein the liner is conditioned for reuse after the VOCs are desorbed.

20. The method of claim 14, wherein the analysis comprises gas chromatography coupled to mass spectrometry and/or other detectors.

21. A method for detecting volatile organic compounds (VOCs) present in an environmental sample, comprising:
collecting an environmental air sample using a device as claimed in claim 1 by
i) positioning a funnel connected to the inlet of the device towards an air space to be sampled; and
ii) powering the device on for a predetermined time;
removing the liner from the device; and
desorbing VOCs adsorbed to the liner for analysis.

22. The method of claim 21, wherein the collecting step is performed for 30-60 minutes.

23. The portable low weight air sampling device of claim 1, wherein the device weighs less than one pound.

24. The method of claim 21, wherein the device comprises a master switch having three positions: switched off, reduced flow, and full flow and the device is set to reduced flow and full flow during the collecting step.

* * * * *